United States Patent [19]

Afseth

[11] Patent Number: 4,795,628

[45] Date of Patent: Jan. 3, 1989

[54] COMPOSITION FOR ORAL HYGIENE

[75] Inventor: John Afseth, Oslo, Norway

[73] Assignee: Blendax-Werke R. Schneider GmbH & Co., Mainz, Fed. Rep. of Germany

[21] Appl. No.: 947,811

[22] Filed: Dec. 30, 1986

[30] Foreign Application Priority Data

Jan. 7, 1986 [DE] Fed. Rep. of Germany ....... 3600165

[51] Int. Cl.$^4$ .......................... A61K 7/16; A61K 7/22; A61K 33/34
[52] U.S. Cl. ........................................ 424/54; 424/49; 424/141
[58] Field of Search ............................ 424/49, 141, 54

[56] References Cited

U.S. PATENT DOCUMENTS 4,662,220 11/1986 Frosch ................................. 424/49

OTHER PUBLICATIONS

Chem. Abst. 78:128425v(1973)-Koeddermann
Chem. Abst. 88 141,894h(1978)-Kunz et al.
Chem. Abst. 95 86330d(1981)-Lukaschek et al.
Chem. Abst. 97:60838s(1982)-Muehlemann et al.
Chem. Abst. 99:218428(m)(1983)-Saxer et al.
Chem. Abst. 105: 164511(e)(1986)-Wile et al.
Chem. Abst. 106: 188988n(1987)-Giertsen et al.

Primary Examiner—Douglas W. Robinson
Attorney, Agent, or Firm—Birch, Stewart, Kolasch & Birch

[57] ABSTRACT

A composition for oral hygiene with efficacy against dental plaque which contains a synergistic mixture of copper compounds and hexetidine, preferably in an amount of about 0.05 to about 1.5 % by weight, calculated based on the total composition.

17 Claims, No Drawings

COMPOSITION FOR ORAL HYGIENE

The present invention relates to a composition for oral hygiene, especially a tooth and mouth care agent having a dental plaque preventing or diminishing activity, containing a mixture of copper compounds and hexetidine as active ingredients.

The use of hexetidine, 1,3-bis(2-ethylhexyl)-5-amino-5-methyl hexahydropyrimidine, as antiseptic ingredient for the treatment of inflammations in the oral and pharyngeal area has been known for a long time.

It has also been tried already to use hexetidine as an agent preventing the formation of dental plaque; however, an effect could not be proven, so that experts came to the opinion that tooth and mouth care agents containing hexetidine are not suitable to prevent the formation of dental plaque.

It is known that the copper cation has an inhibiting effect on dental plaque formation when solutions containing copper compounds are topically brought into contact with the teeth (AADR-Abstracts 1979, No. 117; Caries Research, Vol. 18, 1984, 434–439).

These compounds supplying copper ions do not have the disadvantages known from other plaque-inhibiting compounds on the basis of antimicrobial substances, like e.g. quaternary ammonium compounds or chlorhexidine salts, particularly the discoloration of the teeth after long-term use.

In European Published patent application Nos. 38,867 and 38,868 toothpaste compositions are described which contain copper compounds in a certain composition.

It has now surprisingly been found that this action of the copper compounds against dental plaque even is enhanced when hexetidine is added to such compositions.

Obviously, this is an unexpected synergistic effect. The occurrence of this effect is the more surprising as hexetidine alone has virtually no effect in inhibiting the formation of plaque. So it could not be expected that the action of copper ions which is known per se could still be increased by adding this substance which is not active when used alone.

The amount of copper compounds used in the compositions for oral hygiene according to the invention should be dosed in such a way that about 0.001 to about 1.5% by weight of Cu, calculated to the total composition, is present.

A preferred amount is between 0.01 to 1.0%, particularly from about 0.025 to about 0.1% of Cu.

In principle, all toxicologically safe, mucosa-compatible copper ions, even those which are water-soluble only to a certain degree, are suitable as compounds supplying copper ions.

Inorganic salts are for example:

Copper chloride, $CuCl_2$, and its dihydrate; copper fluoride, $CuF_2$, and its dihydrate; copper fluorosilicate, $CuSiF_6$, and its hexahydrate; copper sulfate, $CuSO_4$, and its pentahydrate; copper nitrate and its tri- and hexahydrate, resp., as well as not so common copper salts such as bromides, bromates, chlorates, iodates, fluorophosphates.

Preferred copper salts of organic acids are acetate, formiate, benzoate, citrate, tartrate, lactate, malate, mandelate, sorbate, pantothenate, gluconate, phytate, glycerophosphate, cinnamate, butyrate, propionate, laurate, oxalate, salicylate.

Also suitable are the copper salts of amino acids, such as glycinate or glutamate. A particularly preferred amino acid salt is copper aspartate.

Hexetidine is contained in the compositions according to the invention in an amount between about 0.025 and about 0.5, particularly 0.05 and 0.25% by weight, calculated to the total composition.

The animal tests described below prove the superior efficiency of a toothpaste containing the mixture according to the invention in comparison to compositions containing one of the substances, i.e. hexetidine and copper sulfate, in analogous concentrations:

20 days old Osborne Mendel rats were divided into 7 groups with 16 animals each and received the plaque standard diet 2000 F.

At the beginning of the test, the animals were inoculated with 0.1 ml of a standardized bacterial suspension of *Actinomyces viscosus* OMZ 105. Further inoculations were carried out each week.

The treatment of the test animals with the preparations to be investigated begins at the 23rd life day, twice daily 0.1 ml test preparation/test animal are applied by a syringe. After 4 weeks the animals were sacrificed and the plaque formation was investigated on the 2 first buccal surfaces and the first 4 lingual surfaces of the molars 1 and 2 in the upper jaw; i.e., 12 surfaces per animal.

The evaluation is carried out after coloration with erythrosin solution according to the following scheme:

0: no plaque
1: up to ⅓ of the surface is covered with plaque.
2: up to ⅔ of the surface are covered with plaque.
3: more than ⅔ of the surface are covered with plaque.

The corresponding points are added and an average value ($\bar{x}$) is calculated.

| Group | $\bar{x}$ | |
|---|---|---|
| 1 | 22.38 | +/− 2.42 |
| 2 | 11.56 | +/− 4.02 |
| 3 | 19.63 | +/− 2.19 |
| 4 | 8.50 | +/− 3.33 |
| 5 | 21.06 | +/− 3.26 |

COMPOSITION OF THE INVESTIGATED PREPARATIONS

Group 1: 2% Hydroxyethyl cellulose gel (placebo).
Group 2: 2% Hydroxyethyl cellulose gel with 0.2% $CuSO_4 \cdot H_2O$ (=0.05% Cu).
Group 3: 2% Hydroxyethyl cellulose gel with 0.5% hexetidine.
Group 4: 2% Hydroxyethyl cellulose gel with 0.20% copper sulfate $5H_2O$ (=0.05% Cu) and 0.05% hexetidine.
Group 5: Untreated control group.

These results show with statistical significance the superiority of the synergistic combination of copper compounds and hexetidine according to the invention in comparison to compositions containing the single components.

The compositions for oral hygiene according to the invention may be used in various application forms. Toothpastes, either opaque or gel-like transparent, mouthwashes, and chewing gum are preferred; however, any other application forms like mouth spray, sucking or chewing tablets, or tooth powders are suitable for this purpose.

A toothpaste may be opaque or transparent. Transparent toothpastes contain polishing agents having the same refraction index as the carrier material.

Especially suitable polishing agents are e.g. alkali aluminum silicates, e.g. zeolites A as disclosed in European Published patent application Nos. 2,690 and 3,023, different calcium phosphates like dicalcium orthophosphate as dihydrate or water-free, calcium carbonate, alumina and its trihydrates, particularly α-alumina trihydrate, tricalcium phosphate, calcium pyrophosphate, insoluble alkali metaphosphates, silicas of different modifications such as silica xerogels, hydrogels or precipitated silica, or powdered plastic materials like polymethyl methacrylate with a particle size distribution between about 0.5 and about 5 μm.

Of course, also mixtures of the mentioned polishing substances may be used, e.g. a mixture of α-alumina hydrate and/or calcium carbonate and synthetic zeolite A in a ratio of about 1:1.

The percentage of polishing agent in a toothpaste according to the invention is preferably between about 20 and about 60% by weight of the total composition.

Of course, it is also possible to use the usual surface-active agents in toothpastes in amounts of up to 2.5% by weight of the total composition.

Suitable synthetic surface-active agents are e.g. alkyl sulfates, alkyl ether sulfates, olefin sulfonates, sodium lauroyl sarcosinate, or ampholytic, nonionic, or cationic compounds or soaps like alkali salts from lauric acid, myristic acid, palmitic acid, stearic acid or mixtures thereof, e.g. coconut oil fatty acids or tallow fatty acids.

The same applies to moisturizers normally present in toothpastes in amounts between about 10 and about 35% by weight. Suitable moisturizers are glycerol, diols like 1,4-butanediol, and 1,2 propanediol, or sugar alcohols like sorbitol, mannitol, or xylitol, and polyglycols with low molecular weights.

Preferred thickening agents are carboxymethyl cellulose and its alkali salts, especially sodium carboxymethyl cellulose, hydroxyalkyl celluloses like hydroxymethyl cellulose and hydroxyethyl cellulose, methyl cellulose, natural gums like tragant, Gum arabicum, Caraya gum, guar gum, Xanthan gum, and Irish moss, synthetic polyelectrolytes like alkali salts of polyacrylic acid as well as inorganic thickening agents, especially colloidal magnesium aluminum silicate or colloidal silica whose amount in toothpastes is between about 0.25 and about 5% by weight, calculated to the total composition.

Suitable fluorine compounds are the different salts of monofluorophosphoric acid such as sodium, potassium, lithium, calcium, and aluminum mono- and difluorophosphate as well as the various ionic fluorides, particularly alkali fluorides like sodium, lithium, potassium, and ammonium fluoride, stannous fluoride, manganese fluoride, copper fluoride, zirconium fluoride, and aluminum fluoride as well as mixtures or adducts of these fluorides, e.g. alkali manganese fluorides.

Further materials which can be used in the preparations for oral hygiene according to the invention are further plaque-inhibiting substances such as zinc salts, substances preventing the formation of dental calculus, such as hydroxy ethane-1,1-diphosphonic acid or alkylene aminotetramethylene phosphonic acids and their water-soluble salts, allantoin, azulen, etc..

A review of compositions to be used in toothpastes as well as of other materials usually applied for the preparation of dental care agents and the manufacturing methods for these compositions are given in the monography of M. S. Balsam and E. Sagarin, "Cosmetics—Science and Technology", 2nd Ed., Vol. 1, p. 423 to 533 (1972), which is included by reference.

The following examples should characterize the principle of the invention:

Example 1 Toothpaste

| | | |
|---|---|---|
| α-Alumina trihydrate (particle size about 1–15 μm) | 58.50 | (% by weight) |
| Sorbitol solution (70%) | 25.50 | |
| Xanthan gum | 0.60 | |
| Sodium monofluorophosphate | 0.80 | |
| Saccharin sodium | 0.10 | |
| Preservative | 0.30 | |
| Sodium lauryl sulfate | 0.40 | |
| Flavour mixture | 0.10 | |
| Copper aspartate | 0.26 | |
| Hexetidine | 0.05 | |
| Water | ad 100.00 | |

Example 2 Toothpaste

| | | |
|---|---|---|
| Synthetic zeolite A $(Na_{12}(AlO_2)_{12}(SiO_2)_{12} \cdot 27\ H_2O$ | 24.00 | (% by weight) |
| Dicalcium orthophosphate | 10.00 | |
| Carboxymethyl cellulose | 1.20 | |
| Sodium lauryl sulfate | 2.00 | |
| Glycerol | 6.00 | |
| Sorbitol | 15.00 | |
| Preservative | 0.30 | |
| Flavour mixture | 1.00 | |
| Colloidal silica | 1.55 | |
| Saccharin sodium | 0.05 | |
| Sodium monofluorophosphate | 0.80 | |
| Copper aspartate | 0.25 | |
| Hexetidine | 0.08 | |
| Water | ad 100.00 | |

Example 3 Toothpaste

| | | |
|---|---|---|
| Irish moss | 0.50 | (% by weight) |
| Xanthan gum | 0.50 | |
| Glycerol | 7.50 | |
| Sorbitol | 22.00 | |
| Copper formiate.4H$_2$O | 0.30 | |
| Copper fluoride (CuF$_2$) | 0.25 | |
| Sodium lauroyl sarcosinate | 1.40 | |
| Cured melamine-formaldehyde condensate (mean particle diameter 1–10 μm) | 28.50 | |
| Titanium dioxide | 0.50 | |
| Saccharin sodium | 0.10 | |
| Flavour mixture | 1.00 | |
| p-Hydroxybenzoic acid methylester | 0.10 | |
| p-Hydroxybenzoic acid n-propylester | 0.05 | |
| Hexetidine | 0.22 | |
| Desalted water | 37.30 | |

Example 4 Toothpaste

| | | |
|---|---|---|
| Irish moss | 0.50 | (% by weight) |
| Xanthan gum | 0.50 | |
| Glycerol | 7.50 | |
| Sorbitol | 28.00 | |
| Copper formiate.4H$_2$O | 0.25 | |
| Hexetidine | 0.10 | |
| Sodium lauroyl sarcosinate | 1.40 | |
| Precipitated silica (Sident ®) | 22.50 | |
| Titanium dioxide | 0.50 | |
| Saccharin sodium | 0.10 | |
| Flavour mixture | 1.00 | |
| p-Hydroxybenzoic acid methylester | 0.10 | |
| p-Hydroxybenzoic acid n-propylester | 0.05 | |
| Desalted water | ad 100.00 | |

Example 5 Toothpaste

| | | |
|---|---|---|
| Xanthan gum | 1.20 | (% by weight) |
| Glycerol | 15.00 | |
| Sorbitol | 12.00 | |

-continued

| | |
|---|---|
| Copper salicylate (Cu(C$_7$H$_5$O$_3$)$_2$.4H$_2$O) | 1.00 |
| Hexetidine | 0.08 |
| Silica xerogel (Syloid ® AL 1, surface about 800 m$^2$/g) | 16.00 |
| Colloidal silica (Aerosil ®) | 3.00 |
| Titanium dioxide | 0.50 |
| Flavour mixture | 1.00 |
| Saccharin sodium | 0.16 |
| Trisodium citrate | 0.25 |
| p-Hydroxybenzoic acid ethyl ester | 0.20 |
| Desalted water | ad 100.00 |

Example 6
Toothpaste

| | |
|---|---|
| Glycerol | 19.00 (% by weight) |
| Sorbitol (70%) | 7.00 |
| Polyethylene glycol 300 | 3.00 |
| Copper lactate hydrate | 1.20 |
| Stannous fluoride (SnF$_2$) | 0.40 |
| Hydroxyethane-1,1-diphosphonic acid, trisodium salt | 1.25 |
| Bromochlorophene | 0.05 |
| Hexetidine | 0.06 |
| Benzoic acid | 0.15 |
| Dehydracetic acid | 0.10 |
| p-Hydroxybenzoic ester n-propylester | 0.05 |
| Polymethyl methacrylate powder (mean particle diameter 3-8 μm) | 20.00 |
| Silica-xerogel (Syloid ® 70, surface about 290 m$^2$/g) | 8.50 |
| Colloidal silica (Aerosil ®) | 1.20 |
| Sodium lauryl ether sulfate (25% in ethanol) | 10.00 |
| Xanthan gum | 0.80 |
| Desalted water | ad 100.00 |

Example 7
Chewing gum

| | |
|---|---|
| Gum base | 2.10 (% by weight) |
| Sorbitol | 25.00 |
| Xylitol | 20.00 |
| Saccharin sodium | 0.30 |
| Hexetidine | 0.30 |
| Copper sulfate.5H$_2$O | 0.50 |
| Glycerol | 2.00 |
| Flavour mixture | 3.70 |
| Ascorbic acid | 1.00 |
| Fructose | 15.00 |

Example 8
Mouthwash concentrate

| | |
|---|---|
| Flavour mixture | 5.00 (% by weight) |
| Copper aspartate | 2.50 |
| Zinc citrate.2H$_2$O | 0.25 |
| Hexetidine | 0.35 |
| Nonionic emulsifier | 1.80 |
| n-Propanol | 5.00 |
| 1-Methoxypropanol(-2) | 35.00 |
| Glycerol | 8.50 |
| Phenyl salicylate | 0.55 |
| Saccharin sodium | 0.30 |
| Water | ad 100.00 |

Before use, the concentrate is diluted with water in a ratio of about 1:4.

Example 9
Chewing gum

| | |
|---|---|
| Gum base | 1.80 |
| Sorbitol | 25.00 |
| Xylitol | 20.00 |
| Saccharin sodium | 0.30 |
| Copper fluoride | 0.50 |
| Copper sulfate.5H$_2$O | 1.30 |
| Hexetidine | 0.50 |
| Glycerol | 2.00 |
| Flavour mixture | 2.70 |
| Ascorbic acid | 1.00 |
| Fructose | 15.00 |

Example 10

-continued

Ready-for-use mouthwash

| | |
|---|---|
| Copper sulfate.5H$_2$O | 0.100 (% by weight) |
| Hexetidine | 0.075 |
| Ethanol | 5.000 |
| Glycerol | 2.500 |
| Nonionic emulsifier | 0.500 |
| Dyestuff, flavour | q.s. |
| Water | ad 100.000 |

When this composition was used twice daily in a clinical double-blind study, a significant reduction of the Plaque Index according to Silness-Löe was observed compared to the efficacy of solutions containing only one of the two components in corresponding concentrations.

What is claimed is:

1. An oral hygiene composition for inhibiting the formation of dental plaque which comprises a mixture of:
   a component for supplying copper ions to the composition such that Cu is present in an amount of about 0.001 to about 1.5% by weight, and
   a hexetidine component in an amount such that hexetidine is present in an amount of 0.025 to 0.5% by weight, wherein the weights are calculated based on the total composition.

2. A composition according to claim 1, wherein said copper ions are present in an amount of about 0.01 to 1.0% by weight.

3. A composition according to claim 1, wherein said copper ions are present in an amount between 0.025 and 0.1% by weight.

4. A composition according to claim 1, wherein said hexetidine is present in an amount between 0.05 and 0.25% by weight.

5. A composition according to claim 3, wherein said hexetidine is present in an amount between 0.05 and 0.25% by weight.

6. A composition according to claim 1, further comprising toothpaste additives, chewing gum additives, or mouthwash additives.

7. A composition according to claim 5, further comprising toothpaste additives, chewing gum additives, or mouthwash additives.

8. A method for preventing the formation of dental plaque which comprises treating teeth with a composition according to claim 1.

9. A method for preventing the formation of dental plaque which comprises treating teeth with a composition according to claim 6.

10. A method for preventing the formation of dental plaque which comprises treating teeth with a composition according to claim 7.

11. A composition according to claim 1, wherein said composition is in the form of a toothpaste.

12. A composition according to claim 1, wherein said composition is in the form of a chewing gum.

13. A composition according to claim 1, wherein said composition is in the form of a mouthwash.

14. A composition according to claim 1, wherein said component for supplying copper ions comprises an inorganic copper salt or an organic copper salt.

15. A composition according to claim 14, wherein said component for supplying copper ions is a member selected from the group consisting of copper chloride, copper fluoride, copper fluorosilicate, copper sulfate, copper nitrate, copper bromide, copper bromate, copper chlorate, copper iodate, and copper flurophosphate.

16. A composition according to claim 14, wherein said component for supplying copper ions is a member selected from the group consisting of copper salts of acetate, formiate, benzoate, citrate, tartrate, lactate, malate, mandelate, sorbate, pantothenate, gluconate, phytate, glycerophosphate, cinnamate, butyrate, propionate, oxalate, and salicylate.

17. A composition according to claim 14, wherein said component for supplying copper ions is a member selected from the group consisting of copper salts of glycinate, glutanate, and aspartate.

* * * * *